US005837484A

United States Patent [19]

Trempe et al.

[11] Patent Number: 5,837,484
[45] Date of Patent: Nov. 17, 1998

[54] STABLE CELL LINES CAPABLE OF EXPRESSING THE ADENO-ASSOCIATED VIRUS REPLICATION GENE

[75] Inventors: James P. Trempe, Toledo, Ohio; Qicheng Yang, San Diego, Calif.

[73] Assignee: Medical College of Ohio, Toledo, Ohio

[21] Appl. No.: 362,608

[22] PCT Filed: Nov. 3, 1994

[86] PCT No.: PCT/US94/12582

§ 371 Date: Jan. 9, 1995

§ 102(e) Date: Jan. 9, 1995

[87] PCT Pub. No.: WO95/13392

PCT Pub. Date: May 18, 1995

Related U.S. Application Data

[63] Continuation of Ser. No. 273,563, Jul. 11, 1994, abandoned, which is a continuation of Ser. No. 151,065, Nov. 9, 1993, abandoned.

[51] Int. Cl.$^6$ .................................................. C12N 15/63
[52] U.S. Cl. ................. 435/69.1; 435/235.1; 435/320.1; 435/369
[58] Field of Search .............................. 435/172.3, 302.1, 435/235.1, 240.2, 69.1, 71.1, 366, 369; 434/93.1, 93.2; 536/23.1, 24.1

[56] References Cited

U.S. PATENT DOCUMENTS

| 4,797,368 | 1/1989 | Carter et al. | 435/320.1 |
| 5,139,941 | 8/1992 | Muzyczka et al. | 435/172.3 |
| 5,141,742 | 8/1992 | Brown et al. | 424/186.1 |
| 5,173,414 | 12/1992 | Lebkowski et al. | 435/172.3 |

FOREIGN PATENT DOCUMENTS

| 4436664 | 7/1996 | Germany. |
| WO 91/18088 | 11/1991 | WIPO. |

OTHER PUBLICATIONS

Carter, B.J., "Adeno–associated virus vectors" *Current Opinion in Biotechnol.* (1992) 3:533–539.

Muzyczka, N., "Use of adeno–associated virus as a general transduction vector for mammalian cells" *Current Topics in Microbiology and Immunology* (1992) 158:97–129.

Flotte, T.R., et al., "Gene expression from adeno–associated virus vectors in airway epithelial cells" *Am. J. Respir. Cell Mol. Biol.* (1992) 7:349–356.

Egan, M., et al., "Defective regulation of outwardly rectifying Cl$^-$ channels by protein kinase A corrected by insertion of CFTR" *Nature* 358:581–584.

Flotte, T.R., et al., "Expression of the cystic fibrosis transmembrane conductance regulator from a novel adeno–associated virus promoter" *J. Biol. Chem.* (1993) 268:3781–3790. An author proof copy is enclosed herewith.

Flotte, T.R., et al., "Stable in vivo expression of the cystic fibrosis transmembrane conductance regulator with an adeno–associated virus vector" *Proc. Natl. Acad. Sci. USA* (1993) 90:10613–10617.

Walsh, C.E., et al., "Regulated high level expression of human γ–globin gene introduced into erythroid cells by an adeno–associated virus vector" *Proc. Natl. Acad. Sci. USA* (1992) 89:7257–7261.

Carter, B.J., et al., "AAV DNA Replication, integration, and genetics" *CRC Handbook of Parvoviruses,* Tijssen, P., ed., (1989) CRC Press, Inc., Boca Raton, FL., vol. I, Chapter 11, pp. 169–226.

Berns, K.I., "Parvoviridae and their replication"*Fields Virology,* Fields, B.N., et al., eds. (1990) Raven Press, New York, NY., vol. 2, pp. 1743–1763.

Dialog™ Computer Abstract (Biosys File) of Srivastava, A., et al., "Nucleotide sequence and organization of the adeno–associated virus 2 genome" *J. Virol.* (1983) 45(2):555–564.

Hermonat, P.L., et al., "Genetics of adeno–associated virus: Isolation and preliminary characterization of adeno–associated virus type 2 mutants" *J. Virol.* (1984) 51(2):329–339.

Tratschin, J.D., et al., "Genetic analysis of adeno–associated virus: Properties of deletion mutants constructed in vitro and evidence for an adeno–associated virus replication function" *J. Virol.* (1984) 51(3):611–619.

Laughlin, C.A., et al., "Spliced adenovirus–associated virus RNA" *Proc. Natl. Acad. Sci. USA* (1979) 76(11):5567–5571.

Tratschin, J.D., et al., "Negative and postitve regulation of trans of gene expression from adeno–associated virus in mammalian cells by a viral rep gene product" *Mol. Cell. Biol.* (1986) 6(8):2884–2894.

Labow, M.A., "Adeno–associated virus gene expression inhibits cellular transformation by heterologous genes" *Mol. Cell. Biol.* (1987) 7(4):1320–1325.

Khleif, S.N., et al., "Inhibition of cellular transformation by the adeno–associated virus rep gene" *Virology* (1991) 181:738–741.

Mendelson, E., et al., "Expression and rescue of a nonselected marker from an integrated AAV vector" *Virology* (1988) 166:154–165.

Vincent, K.A., et al., "Replication and packaging of HIV envelope genes in a novel adeno–associated virus system" *Vaccines 90* (1990) Cold Spring Harbor Laboratory Press, pp. 353–359.

Samulski, R.J., et al., "Cloning of adeno–associated virus into pBR322: Rescue of intact virus from the recombinant plasmid in human cells"*Proc. Natl. Acad. Sci. USA* (1982) 79:2077–2081.

(List continued on next page.)

*Primary Examiner*—James Ketter
*Assistant Examiner*—Irem Yucel
*Attorney, Agent, or Firm*—Morrison & Foerster

[57] ABSTRACT

Stable packaging cell lines derived from human 293 cells which are transfected with an AAV vector having the AAV rep gene operably line to a heterologous transcription promoter, such as the metallothionein promoter, or an AAV Rep78 insensitive homologous promoter and which are capable of producing AAV Rep proteins and being useful for packaging recombinant AAV vectors containing target polynucleotides.

18 Claims, 6 Drawing Sheets

OTHER PUBLICATIONS

Laughlin, C.A., et al., "Cloning of infectious andeno–associated virus genomes in bacterial plasmids" *Gene* (1983) 23:65–73.

Senapathy, P. et al., "Molecular cloning of adeno–associated virus variant genomes and generation of infectious virus by recombination in mammalian cells" *J. Biol. Chem.* (1984) 259(7):4661–4666.

Tratschin, J.D., et al., "A human parvovirus, adeno–associated virus, as a eucaryotic vector: Transient expression and encapsidation of the procaryotic gene for chloramphenicol acetyltransferase" *Mol. Cell. Biol.* (1984) 4(10):2072–2081.

Hermonat, P.L., et al., "Use of adeno–associated virus as a mammalian DNA cloning vector: Transduction of neomycin resistance to mammalian tissue culture cells" *Proc. Natl. Acad. Sci. USA* (1984) 81:6466–6470.

Tratschin, J.D., et al., "Adeno–associated virus vector for high–frequency integration, expression, and rescue in genes in mammalian cells" *Mol. Cell. Biol.* (1985) 5(11):3251–3260.

McLaughlin, S.K., "Adeno–associated virus general transduction vectors: Analysis of proviral structures" *J. Virol.* (1988) 62(6):1963–1973.

Lebkowski, J.S., et al., "Adeno–associated virus: a vector system for efficient introduction and integration of DNA into a variety of mammalian cell types" *Mol. Cell. Biol.* (1988) 8(10):3988–3996.

Carter, B.J., et al., "Parvoviruses as vectors" *CRC Handbook of Parvoviruses,* Tijssen, P., ed., (1989) CRC Press, Inc., Boca Raton, FL., vol. II, Chapter 18, pp. 247–284.

Samulski, R.J., et al., "Helper–free stocks of recombinant adeno–associated viruses: Normal integration does not require viral gene expression" *J. Virol.* (1989) 63(9):3822–3828.

LaFace, D., et al., "Gene transfer hematopoietic progenitor cells mediated by an adeno–associated virus vector" *Virology* (1988) 162:483–486.

Samulski, R.J., et al., "A recombinant plasmid from which an infectious adeno–associated virus genome can the excised in vitro and its use to study viral replication" *J. Virol.* (1987) 61(10):3096–3101.

Srivastava, C.H., et al., "Construction of a recombinant human parvovirus B19: Adeno–associated virus 2(AAV) DNA inverted terminal repeats are functional in an AAV–B19 hybrid virus" *Proc. Natl. Acad. Sci. USA* (1989) 86:8078–8082.

Chatterjee, S., et al., "Transduction of intracellular resistance to HIV production by adeno–associated virus–based antisense vector" *Vaccines 91* (1991) Cold Spring Harbor Laboratory Press, pp. 85–90.

Wong, K.K., et al., "Restriction of HSV–1 production in cell lines transduced with an antisense viral vector targeting the ICP4 gene" *Vaccines 91* (1991) Cold Spring Harbor Laboratory Press, pp. 183–189.

Chatterjee, S., et al., "Dual–target inhibition of HIV–1 in vitro by means of an adeno–associated virus antisense vector" *Science* (1992) 258:1485–1488.

Muro–Cacho, C.A., et al., "Gene transfer in human lymphocytes using a vector based on adeno–associated virus" *J. Immunol.* (1992) 11:231–237. An author proof is enclosed herewith.

Antoni, B.A., et al., "Adeno–associated virus rep protein inhibits human immunodeficiency virus type 1 production in human cells" *J. Virol.* (1991) 65(1):396–404.

Kotin, R.M., et al., "Characterization of a preferred site on human chromosome 19q for integration of adeno–associated virus DNA by non–homologous recombination" *EMBO J.* (1992) 11(13):5071–5078.

Labow, M.A., et al., "Positive and negative autoregulation of the adeno–associated virus type 2 genome" *J. Virol.* (1986) 60(1):251–258.

Winocour, E., et al., "Modulation of the cellular phenotype by integrated adeno–associated virus" *Virology* (1992) 190 316–329.

Yang et al., "Characterization of cell lines that inducibly express the adeno–associated virus Rep. proteins" *J. Virol.* (1994) 68(8):4847–4856.

Flotte et al., "An improved system for packaging recombinant adeno–associated virus vectors capable of in vivo transduction" *Gene Therapy* (1995) 2(1):29–37.

STABLE CELL LINES CAPABLE OF EXPRESSING THE ADENO-ASSOCIATED VIRUS REPLICATION GENE

This application is a 371 of PCT/US94/12582, filed Nov. 3, 1994, which is a continuation of U.S. application Ser. No. 08/273,563, filed Jul. 11, 1994, now abandoned, which is a continuation of U.S. application Ser. No. 08/151,065, filed Nov. 9, 1993, now abandoned.

ACKNOWLEDGEMENT OF SUPPORT

This invention was made with support from: (i) the United States Government under R29 CA 58743 from the National Institutes of Health; (ii) the March of Dimes Birth Defects Foundation under 1-FY92-0527; and (iii) the Ohio Cancer Research Associates. These three agencies have certain rights in the invention.

TECHNICAL FIELD

This invention relates to gene therapy and more specifically to stable cell lines that are useful for packaging recombinant adeno-associated virus type 2 (AAV) vectors without producing wild-type AAV.

BACKGROUND

AAV vectors are among a small number of recombinant virus vector systems which have been shown to have utility as in vivo gene transfer agents (reviewed in Carter, 1992, *Current Opinion in Biotechnology*, 3:533–539; Muzcyzka, 1992, *Curr Top. Microbiol. Immunol.* 158:97–129) and thus are potentially of great importance for human gene therapy. AAV vectors are capable of high-frequency stable DNA integration and expression in a variety of cells including cystic fibrosis (CF) bronchial and nasal epithelial cells (Flotte et al., 1992a, *Am. J. Respir. Cell Mol. Biol.* 7:349–356; Egan et al., 1992, *Nature,* 358:581–584; Flotte et al., 1993a, *J. Biol. Chem.* 268:3781–3790; Flotte et al., 1993b, *Proc. Natl. Acad. Sci. USA,* (1993) 90:10613–10617), human bone marrow-derived erythroleukemia cells (Walsh et al., 1992, *Proc. Natl. Acad. Sci. USA,* 89:7257–7261), and several others. AAV may not require active cell division for stable expression which would be a clear advantage over retroviruses, especially in tissue such as the human airway epithelium where most cells are terminally differentiated and non-dividing.

AAV is a defective parvovirus that grows only in cells in which certain functions are provided by a co-infecting helper virus. General reviews of AAV may be found in Carter, 1989, *Handbook of Parvoviruses,* Vol. 1, pp. 169–226, Carter, 1989, *Handbook of Parvoviruses,* Vol II, pp. 247–281, Berns, 1990, *Virology, pp.* 1743–1764, Raven Press, N.Y.). Examples of co-infecting viruses that provide helper functions for AAV growth and replication are adenoviruses, herpesviruses and in some cases poxviruses such as vaccinia. The nature of the helper function is not known but appears to be some indirect effect of the helper virus which renders the cell permissive for AAV replication. This concept is supported by the observation that in certain cases AAV replication may occur at a low level of efficiency in the absence of helper virus co-infection if the cells are treated with agents that are either genotoxic or that disrupt the cell cycle.

AAV has a very broad host range with neither obvious species or tissue specificity and will replicate in virtually any cell line of human, simian or rodent origin provided an appropriate helper is present. AAV is ubiquitous and has been isolated from a wide variety of animal species including most mammalian and several avian species.

AAV has not been identified as the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector because most of the other viral systems proposed for this application such as retroviruses, adenoviruses, herpesviruses, or poxviruses are disease-causing viruses.

The AAV genome has one copy of the 145-nucleotide-long ITR (inverted terminal repeat) on each end and a unique sequence region of about 4470 nucleotides long (Srivastava et al., 1983, *J. Virol.,* 45:555–564) that contains two main open reading frames for the rep and cap genes (Hermonat et al., *J. Virol.* 51:329–339; Tratschin et al., 1984a, *J. Virol.,* 51:611–619). The unique region contains three transcription promoters $p_5$, $P_{19}$, and $p_{40}$ (Laughlin et al., 1979, *Proc. Natl. Acad. Sci. USA,* 76:5567–5571) that are used to express the rep and cap genes. The ITR sequences are required in cis and are sufficient to provide a functional origin of replication (ori) and also are sufficient to provide signals required for integration into the cell genome as well as for efficient excision and rescue from host cell chromosomes or from recombinant plasmids. In addition, it has been shown that the ITR can function directly as a transcription promoter in an AAV vector (Flotte et al., 1993, vide supra).

The rep and cap genes are required in trans to provide functions for replication and encapsidation of viral genome, respectively. The rep gene is expressed from two promoters, $p_5$ and $P_{19}$. Transcription from $p_5$ yields an unspliced 4.2 kb MRNA which encodes a protein, Rep78, and a spliced 3.9 kb mRNA which encodes a protein, Rep68. Transcription from $P_{19}$ yields an unspliced MRNA which encodes Rep52 and a spliced 3.3 kb mRNA which encodes Rep40. Thus, the four Rep proteins all comprise a common internal region sequence but differ with respect to their amino and carboxyl terminal regions. Only Rep78 and Rep68 are required for AAV duplex DNA replication, but Rep52 and Rep40 appear to be needed for progeny, single-strand DNA accumulation. Mutations in Rep78 and Rep68 are phenotypically Rep– whereas mutations affecting only Rep52 and Rep40 are Rep+ but Ssd–. Rep68 and Rep78 bind specifically to the hairpin conformation of the AAV ITR and possess several enzyme activities required for resolving replication at the AAV termini. Rep52 and Rep40 have none of these properties.

The Rep proteins, primarily Rep78 and Rep68, exhibit several pleiotropic regulatory activities including positive and negative regulation of AAV genes and expression from some heterologous promoters, as well as inhibitory effects on cell growth (Tratschin et al., 1986, *Mol. Cell. Biol.* 6:2884–2894; Labow et al., 1987, *Mol. Cell. Biol.,* 7:1320–1325; Khleif et al., *Virology,* 181:738–741). The AAV $p_5$ promoter is negatively autoregulated by Rep78 or Rep68 (Tratschin et al., 1986, *Mol. Cell. Biol.* 6:2884–2894).

The general principles of AAV vector construction were defined as reviewed recently (Carter, 1992, *Current Opinion in Biotechnology,* 3:533–539; Muzyczka, 1992, *Current Topics in Microbiology and Immunology,* 158:97–129). AAV vectors are constructed in AAV recombinant plasmids by substituting portions of the AAV coding sequence with foreign DNA to generate a vector plasmid. In the vector plasmid, the terminal (ITR) portions of the AAV sequence must be retained intact because these regions are required in cis for several functions, including excision from the plasmid after transfection, replication of the vector genome and integration and rescue from a host cell genome. The vector can then be packaged into an AAV particle to generate an AAV transducing virus by transfection of the vector plasmid into cells that are infected by an appropriate helper virus such as adenovirus or herpesvirus. In order to achieve replication and encapsidation of the vector genome into AAV particles, the vector plasmid must be complemented for any AAV functions required in trans, namely rep and cap, that were deleted in construction of the vector plasmid.

As discussed, AAV vectors have potential utility for treatment of human disease by gene therapy. One of the limiting factors for AAV gene therapy has been the relative inefficiency of the vector packaging systems that have been used. Because of the lack of cell lines expressing the AAV trans complementing functions, such as rep and cap, packaging of AAV vectors has been achieved in adenovirus-infected cells by co-transfection of a packaging plasmid and a vector plasmid. The efficiency of this process may be limited by the efficiency of transfection of each of the plasmid constructs, and by the level of expression of Rep proteins from the packaging plasmids described to date. Each of these problems appears to relate to the biological activities of the AAV Rep proteins. In addition, and as noted above, all of the packaging systems described above have the ability to generate wild-type AAV by recombination.

The lack of cell lines stably expressing functional Rep apparently reflects a cytotoxic or cytostatic function of Rep as shown by the inhibition by Rep of neo-resistant colony formation (Labow et al., 1987; Trempe et al., 1991). This also appears to relate to the tendency of Rep to reverse the immortalized phenotype in cultured cells, which has made the production of cell lines stably expressing functional Rep extremely difficult. Several attempts to generate cell lines expressing Rep have been made. Mendelson et al., (1988, *Virology*, 166:154–165) reported obtaining very low level expression of certain AAV Rep proteins after stable transfection of HeLa or 293 cells with plasmids containing an AAV rep gene, but the level was insufficient for vector production. Vincent et al., (1990, *Vaccines* 90, Cold Spring Harbor Laboratory Press, pp. 353–359) attempted to generate cell lines containing the AAV rep and cap gene expressed from the normal AAV promoters, but these attempts were not successful either because the vectors were contaminated with a 100-fold excess of wild-type AAV particles or because the vectors were produced at only very low titers of less than $4 \times 10^3$. In an alternate approach, Lebkowski et al. (U.S. Pat. No. 5,173,414, issued Dec. 22, 1992) constructed cell lines containing AAV vectors in an episomal plasmid. These cell lines could then be infected with adenovirus and transfected with the trans complementing AAV functions rep and cap to generate preparations of AAV vector. It is claimed that this allows higher titers of AAV stocks to be produced. However, in the examples shown, the only information relative to titer is that one human cell line, K562, could be transduced at efficiencies of only 1% or less, which does not indicate high titer production of any AAV vector. In this system the vector is carried as an episomal (unintegrated construct), and it is stated that integrated copies of the vector are not preferred.

The approach to packaging of AAV vectors described by Lebkowski et al., 1992, has several undesirable aspects. First, maintaining the vector as an unintegrated, high copy number episomal plasmid in a cell line is not desirable because the copy number per cell cannot be rigorously controlled, and episomal DNA is much more likely to undergo rearrangement leading to production of defective vectors. Secondly, in this system, the vector must still be packaged by infecting the cell line with adenovirus and introducing a plasmid containing the AAV rep and cap genes. The plasmid used by Lebkowski et al., 1992, again was pBa1 which, as noted above, has overlapping homology with the vector ITR sequences and will result in generation of wild-type AAV. Third, in the pBa1 packaging plasmid used by Lebkowski et al., 1988, 1992, the rep gene is expressed off its homologous $p_5$ promoter and is thus negatively autoregulated and therefore rep expression is likely to be limited.

The problem of suboptimal levels of rep expression after plasmid transfection may relate to another biological activity of these proteins. There is evidence (Tratschin et al., 1986, *Mol. Cell. Biol.* 6:2884–2894) that AAV-Rep proteins down-regulate their own expression from the AAV-$p_5$ promoter which has been used in all of the previously described packaging constructs such as pAAV/Ad (Samulski et al., 1989) or pBa1 (Lebkowski et al., 1988, 1992).

The present invention provides stable cell lines that are capable of relatively high levels of Rep78 and are useful for packaging AAV vectors without producing wild-type AAV.

DISCLOSURE OF THE INVENTION

One aspect of the invention is a stable cell line having an AAV vector having the rep gene operably linked to a heterologous promoter or a Rep78 insensitive transcription promoter, said cell line being capable of producing functional Rep78.

Another aspect of the invention is a method of packaging a recombinant AAV vector without producing wild-type AAV comprising transfecting the above-described cell line which has been infected with a helper virus with a recombinant AAV vector, said AAV vector being capable of expressing the AAV cap gene or being complemented with a second vector capable of expressing the AAV cap gene but lacking overlapping homology with AAV sequences in the above-described cell line, and culturing the transfected cells under conditions which permit expressing of the rep and cap genes.

Still another aspect of the invention is a method for producing the above-described stable cell line comprising transfecting a mammalian cell line capable of infection by AAV with an AAV vector having the rep gene operably linked to a heterologous promoter or a Rep78 insensitive transcription promoter, culturing the transfected cells under conditions that permit expression of the rep gene, selecting a cell that stably produces Rep78 from the culture, and growing said cell to produce the cell line.

μl of nuclear extract from pCDM8 (lane pCDM8) or pCD-Mrep (lane pCDMrep) transfected 293 cells, or from induced (+) or uninduced (−) neo5 or neo6 cells.

Figure 4:
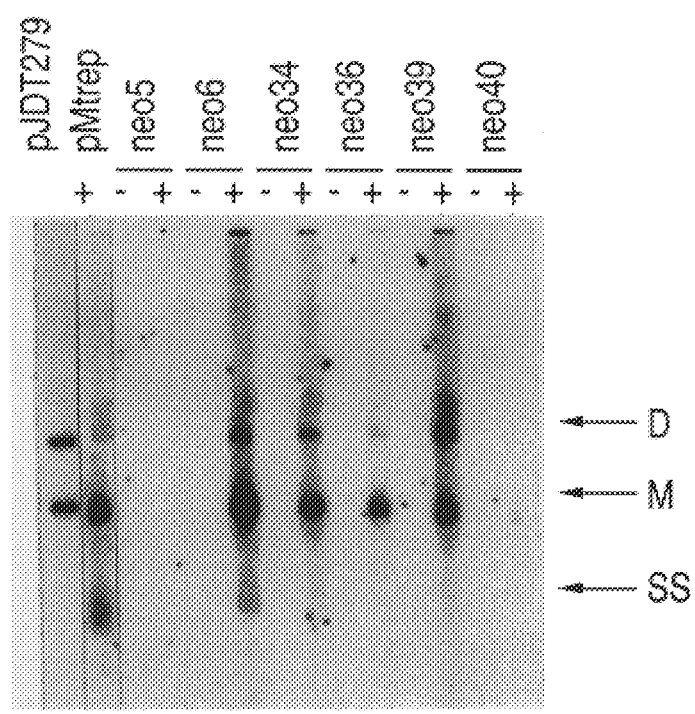

FIG. 4 is a half-tone reproduction of Southern hybridization analysis of a packaging assay for a rep gene mutant AAV genome in the presence (+), or absence (−) of induction.

Figure 5:
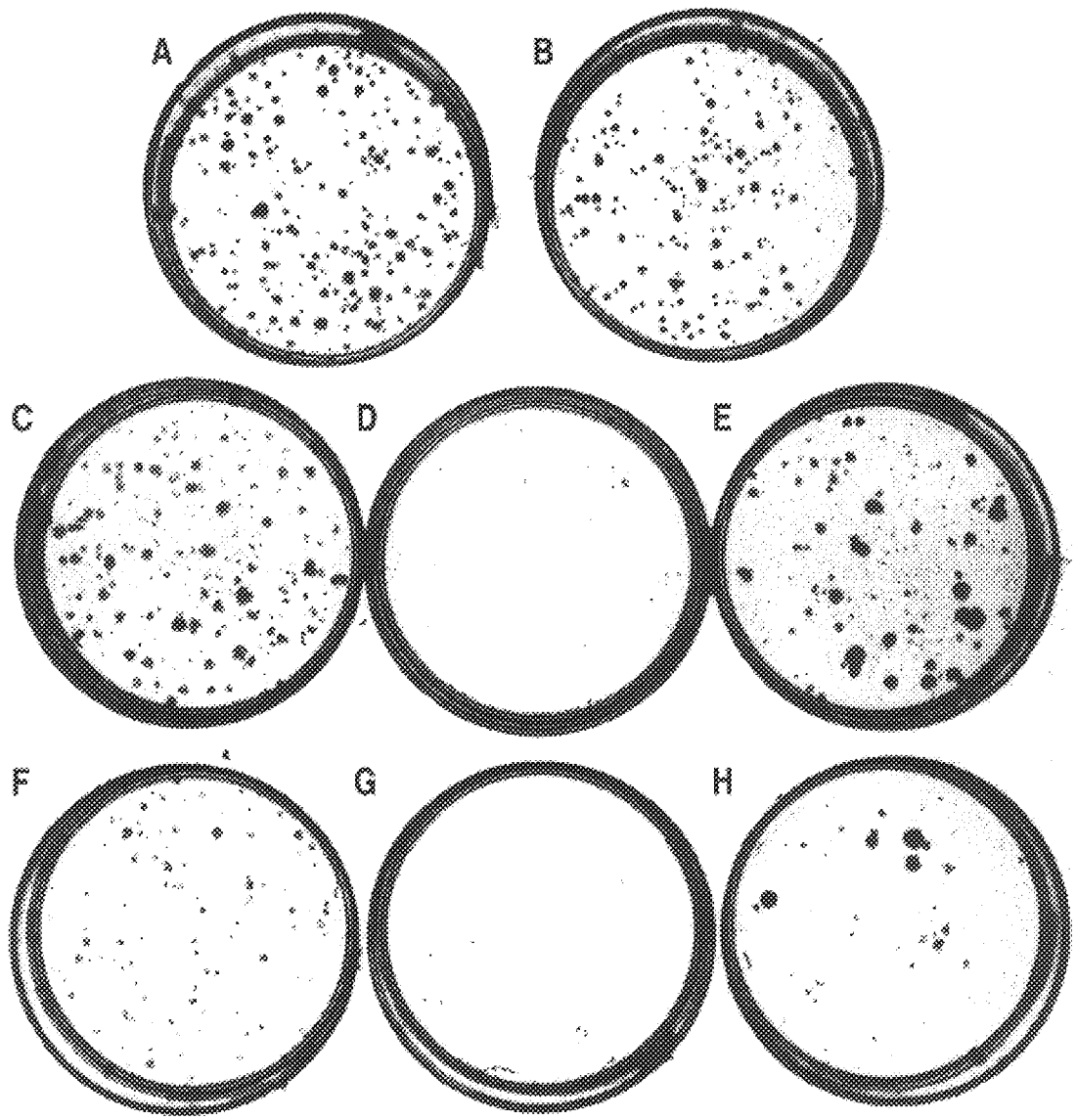

FIG. 5 is a half-tone photograph of plates from the colony forming efficiency (CFE) assay.

Figure 6A:
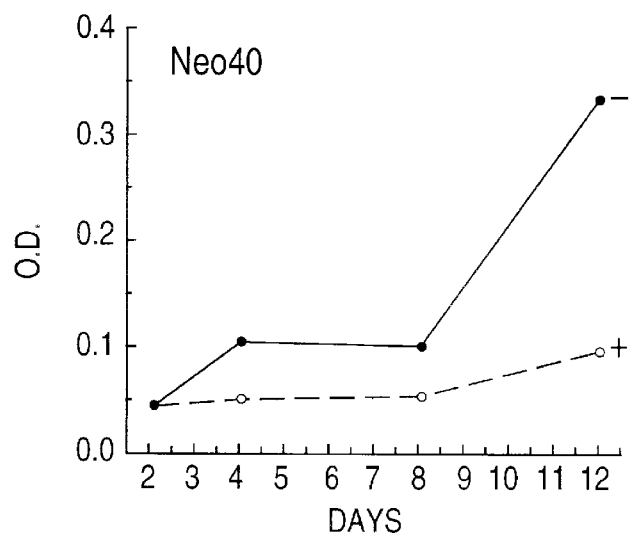
Figure 6B:
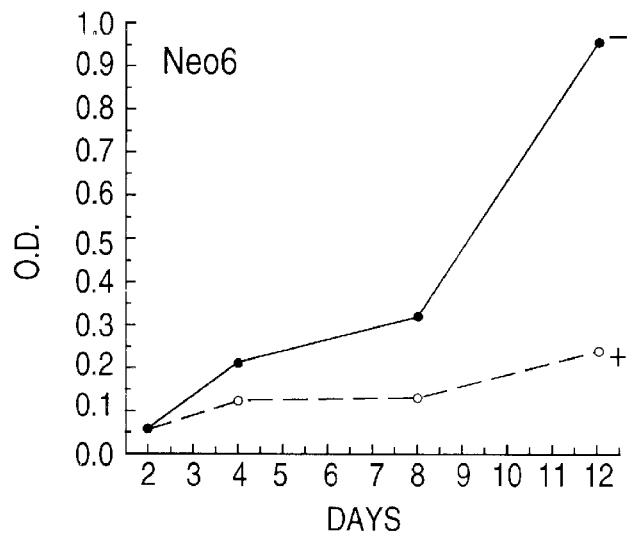
Figure 6C:
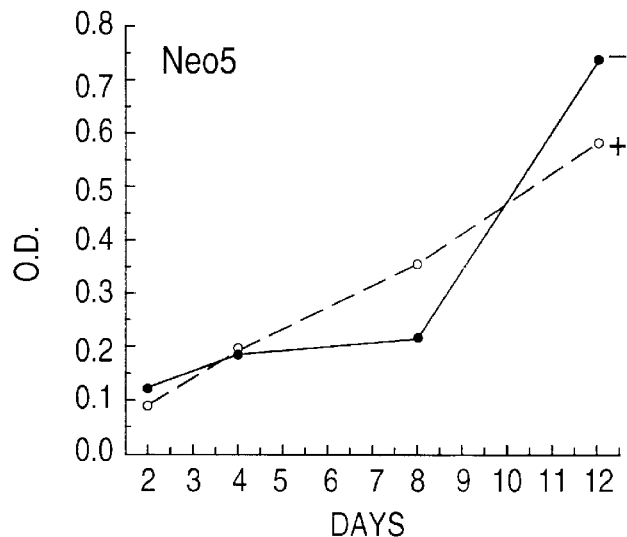

FIG. 6 is a graph displaying the results of the MTT growth assay. The cell growth curves in the presence (+) or absence (−) of heavy metal induction were derived from four experiments. The results are expressed as optical densities (O.D.) vs. time after plating (days).

MODES FOR CARRYING OUT THE INVENTION

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, *Molecular Cloning: A Lab Manual,* Second Edition (1989), *Oligonucleotide Synthesis* (M. J. Gait Ed., 1984), *Animal Cell Culture* (R. I. Freshney, Ed., 1987), the series *Methods in Enzymology* (Academic Press, Inc.); *Gene Transfer Vectors for Mammalian Cells* (J. M. Miller and M. P. Calos eds. 1987), *Handbook of mental Immunology,* (D. M. Weir and C. C. Blackwell, Eds.), Current Protocols in Molecular Biology (F. M. Ausubel, R. Brent, R. E. Kingston, D. D. Moore, J. G. Siedman, J. A. Smith, and K. Struhl, eds., 1987), and Current Protocols in Immunology (J. E. Coligan, A. M. Kruisbeek, D. H. Margulies, E. M. Shevach and W. Strober, eds., 1991). All patents, patent applications, and publications mentioned herein, both supra and infra, are hereby incorporated herein by reference.

The cell lines of the invention may be derived from any mammalian parent cell line that is susceptible to AAV infection. As indicated previously, AAV has a very broad host range and has been isolated from a variety of mammalian cell types including simian, human and rodent cells. For gene therapy, human cell lines in which appropriate helper functions can be expressed will be used. Examples of such human cell lines from which the invention cell lines may be derived are 293, HeLa, A549, KB, Detroit and WI38. 293 cells are particularly preferred.

The cell lines of the invention are produced by transfecting the parent cell line with a plasmid having the AAV rep gene operably linked to a heterologous promoter or an AAV Rep78 insensitive promoter, culturing the transfected cells in a selective medium, culturing the surviving cells under conditions that promote expression of the AAV rep gene, selecting cells that produce Rep78, and culturing the Rep78-producing cells.

The plasmid containing the rep gene that is used to transfect the parent cells should be capable of stably integrating into the cell and should not be rescued by infection of the transfected cell with a helper virus. It includes the AAV rep gene operatively linked to a heterologous transcription promoter. The promoter can be homologous, but it must be Rep78 insensitive, at least to the extent that it is not completely down-regulated by the expressed Rep78 protein. Acceptable promoters may be somewhat, but not strongly, downregulated by rep gene expression. The promoter may be an inducible promoter or a constitutive promoter. Examples of inducible promoters include the following: heavy metal ion inducible promoters such as the metallothionein promoter; steroid hormone inducible promoters, such as the MMTV promoter, or the growth hormone promoter; promoters which would be inducible by the helper virus such as adenovirus early gene promoter inducible by adenovirus E1A protein, or the adenovirus major late promoter; herpesvirus promoter inducible by herpesvirus proteins such as VP16 or 1CP4; vaccinia or poxvirus inducible promoters or promoters inducible by a poxvirus RNA polymerase; bacterial promoter such as that from T7 phage which would be inducible by a poxvirus RNA polymerase; or a bacterial promoter such as that from T7 RNA polymerase. Strong constitutive promoters that will be suitable for use as the heterologous promoter for rep expression include the adenovirus major later promoter, the cytomegalovirus immediate early promoter, the β actin promoter, or the β globin promoter. Promoters activated by RNA polymerase III could also be used.

In the examples shown infra, the parent cells were cotransfected with a neo gene-containing vector and the initial selection was performed by culturing in a geneticin-containing medium. It is, of course, apparent that other selective markers may be used. After initial selection, surviving cells are isolated, cultured under conditions permitting the expression of the rep gene (e.g., in the case of inducible promoters, including an inducing agent in the culture medium), harvested, and assayed for Rep78 production. Western blotting or other suitable assays may be used. Clones producing Rep78 are expanded to produce the inventive cell lines (the term "cell line" is intended to include progeny (subclones) of an original line). Stability is manifested by the ability to produce Rep78 over at least about 12 months and greater than about 50 passages. The level of Rep78 protein production by the cells is sufficient to permit the cells to be used to package recombinant AAV vectors. Following the inventive method, packaged vectors have been measured in the supernatant at titers ranging from $2.8 \times 10^7$ to $1.4 \times 10^8$ viral particles per milliliter. These supernatant titers compare very well with the prior art, even though the prior art generally has reported levels after concentration procedures.

The packaging cell lines of the invention are used to package recombinant AAV vectors as follows.

The recombinant AAV vector is comprised of the AAV ITR regions and a transcription promoter operably linked to a target polynucleotide. The transcription promoter that is linked to the target polynucleotide allows the formation of transcripts, and includes, for example, non-AAV promoters as well as AAV promoters such as p5, $p_{19}$, $p_{40}$, and AAV ITR promoters. The transcription and/or translation products of the target polynucleotide are of use, preferably in gene therapy. Thus, target polynucleotides include genes to be delivered for gene therapy, for example, those encoding subunit chains of hemoglobin, enzymes, proteins such as the cystic fibrosis transmembrane conductance regulator (CFTR), and the like. Target polynucleotides may also be polynucleotides that when transcribed have activity as antisense molecules, as decoys that bind to transcription or translation factors, as ribozymes, and the like. Target polynucleotides also include genes that encode immune response modulators such as cytokine and major histocompatibility genes. Another class of polynucleotides that can be used for gene therapy are genes that make the recipient cell susceptible to specific drugs such as the herpes virus thymidine kinase gene and methotrexate-resistant, mutane dihydrofolate reductase genes. Another target polynucleotide is wild-type p53 tumor suppressor cDNA for replacement therapy of the missing or damaged p53 gene which is associated with lung, breast and other types of cancer.

The cells are infected with a helper virus such as adenovirus or herpes virus and then transfected with the vector. Other means of introducing the vector, e.g., electroporation, may be used. Complementing AAV capsid function is provided by cotransfecting the cells with a vector that is capable of expressing the AAV cap gene. The complementing vector may express the cap gene from either a homologous AAV promoter such as the $p_{40}$ promoter or from a heterologous promoter. Alternatively, the AAV cap gene may be included in the primary vector, thus eliminating the need for a complementing vector. To avoid the development of wild-type AAV, the transfecting AAV vector must have no overlapping homology with AAV sequences already in the cells infected with the helper virus.

After transfection the cells are cultured under conditions which permit expression of the rep and cap genes and replication of AAV. If the rep gene is operably linked to an inducible promoter, a suitable inducing agent is included in the medium. The cells are typically grown for 2–5 days, lysates are prepared, and the recombinant AAV vector particles are purified by techniques known in the art.

The following examples further illustrate the invention. They are not intended to limit the invention in any manner.

The neo6 cell line, described below, was deposited on Nov. 9, 1993, with the American Type Culture Collection (ATCC), 12301 Parklawn Dr., Rockville, Md. 20852, and has been assigned the Accession Number CRL 11484. The deposit was made under the terms of the Budapest Treaty. Upon allowance and issuance of this application as a United States Patent, all restriction on availability of the deposit will be irrevocably removed; and access to the designated deposits will be available during pendency of the above-named application to one determined by the Commissioner to be entitled thereto under 37 CFR § 1.14 and 35 USC § 1.22. Moreover, the designated deposits will be maintained for a period of thirty (30) years from the date of deposit, or for five (5) years after the last request for the deposit; or for the enforceable life of the U.S. patent, whichever is longer. The deposited materials mentioned herein are intended for convenience only, and are not required to practice the present invention in view of the descriptions herein, and in addition these materials are incorporated herein by reference.

EXAMPLES

Example 1
Production of Plasmids

Figure 1:
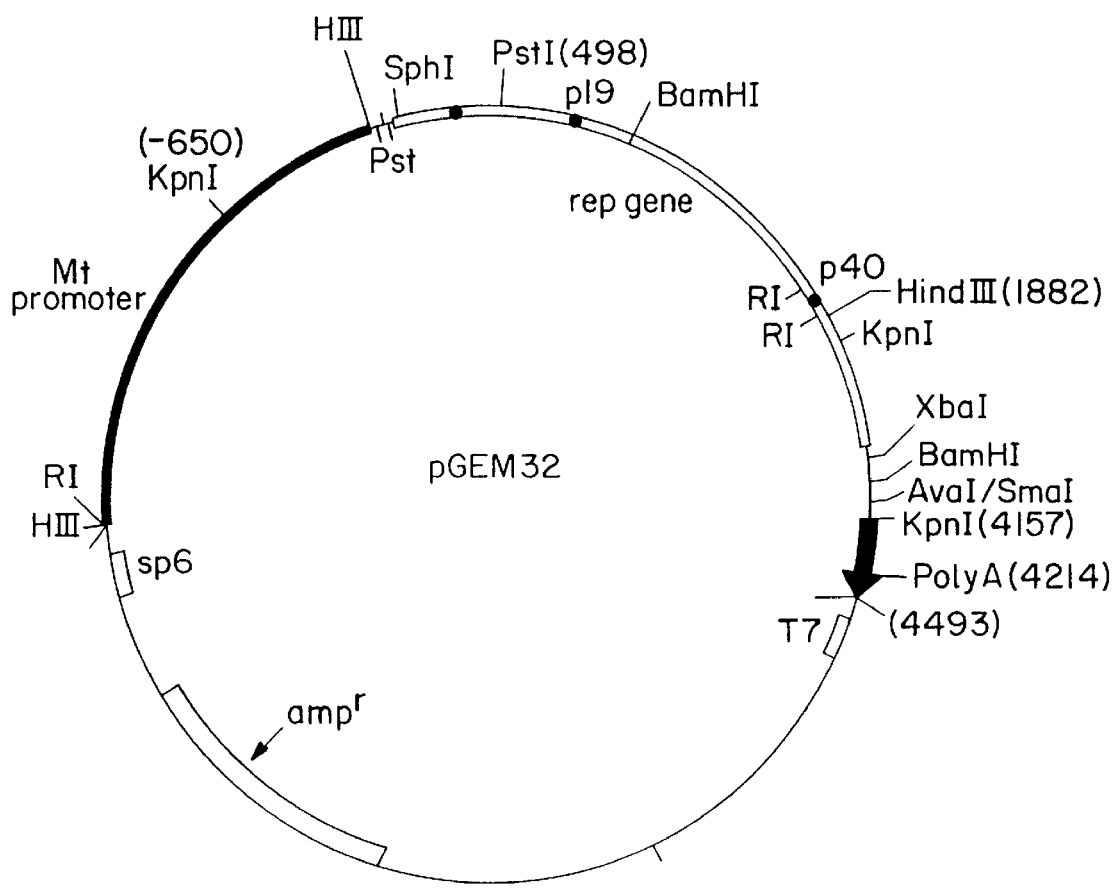
FIG. 1 is a representation of the pMtrep plasmid.

Standard procedures were followed for plasmid construction, growth and purification (Ausubel et al. (ed.) 1987. *Current Protocols in Molecular Biology.* Greene Publishing Associates, Brooklyn, N.Y.). Adenovirus type 2 was used at a multiplicity of infection (MOI) of 5. Plasmid pMtrep (FIG. 1) contains the wild type rep gene from deoxyribonucleotide 263 to 2233 of the AAV genome operably linked to a 1.9 kbp DNA fragment from the mouse metallothionein I gene that contains a heavy metal-inducible transcription promoter (Hamer and Walling. 1982. *J. Mol. Appl. Genet.* 1:273–288.; Yang et al. 1992. *J. Virol.* 66:6058–6069). Plasmid pCDMrep contains the same rep gene sequence inserted into the pCDM8 vector (Invitrogen Corp.) (Yang and Trempe. 1993. *J. Virol.* 67:4442–4447).

Plasmid pΔMtrep was constructed by performing a partial KpnI digestion of pMtrep and isolating a 2725 bp fragment that contained the mouse metallothionein I promoter from the KpnI site at −650 bp from the transcription start site to 69 bp downstream of the start site, approximately 18 bp of pGEM3Z polylinker sequence (from the HindIII to the XhoI sites), the AAV rep gene sequences contained in the AvaI restriction endonuclease fragment from 263–2233 in the AAV genome, and approximately 21 bp of pGEM3Z polylinker sequence (from the XhoI to the KkpnI sites). The 2725 bp KpnI fragment was inserted in the KpnI site of the plasmid pAW1 to create pΔMtrep. Plasmid pAW1 was created by inserting a 336 bp KpnI to SnaBI fragment, containing the AAV polyadenylation signal from pAV2, into the EcoRI to KpnI sites of pGEM3Z after the EcoRI site had been converted to a blunt end with the Klenow fragment of *E. coli* DNA polymerase I. Thus, pΔMtrep contains 69 bp of the leader sequence of the mouse metallothionein mRNA and the immediate upstream regulatory elements that allow for heavy metal induction, but pΔMtrep lacks the upstream enhancer elements from the promoter.

Plasmid pJDI279 contains the complete AAV2 genome but with a frame shift mutation in the rep gene at the SstI site at nucleotide 814 (Tratschin et al. 1984. *J. Virol.* 51:611–619.). Plasmid pSV2neo has been described previously (Southern and Berg. 1982. *J. Mol. Appl. Genet.* 1:327–341).

Example 2
Production of inducible cell lines expressing the Rep proteins

Human 293 cells (Graham et al. 1977. *J. Gen. Virol.* 36:59–72) were grown in Eagle minimum essential medium (MEM) supplemented with antibiotics and 10% fetal bovine serum. All DNA transfections were carried out on cultures that were 50–70% confluent using the calcium phosphate method one day after plating cells onto culture dishes (Ausubel et al. (ed.) 1987. *Current Protocols in Molecular Biology,* Greene Publishing Associates, Brooklyn, N.Y.).

The inhibition of cell proliferation mediated by the AAV rep gene has prevented the development of cell lines that express significant levels of Rep proteins. To circumvent these antiproliferative effects, the rep gene was operably linked to the inducible mouse metallothionein I (Mt) transcription promoter (Yang et al. 1992. *J. Virol* 66:6058–6069). The Mt promoter fragment used in the construction of pΔMtrep contains 64 bp of the first exon of the metallothionein gene to −650 in the promoter. This promoter has reduced basal level expression but retains its heavy metal inducibility (KARIN). pΔMtrep and pSV2neo were cotransfected onto 293 cells, and geneticin was used to select those cells that had acquired and expressed the neo gene. Geneticin-resistant clones were screened for the production of Rep proteins upon induction. $2 \times 10^5$ human 293 cells in 35 mm dishes were co-transfected with 2 µg of pSV2neo and 6 µg of pΔMtrep. Inducible cell lines were grown in MEM medium containing 10% dialyzed FBS and 1 mg/ml (600 µg/ml active component) of geneticin (Sigma Chem. Co.). All cells were maintained as monolayer culture at 37° C. in a 5.0% $CO_2$ atmosphere. Two days later, cells were trypsinized, diluted and plated on 100 mm dishes to allow for outgrowth of single cell clones. Selective medium containing 0.6 mg/ml of active component geneticin (Sigma Chemical Corp.) in MEM was put on cells 48 hr later.

Figure 2:
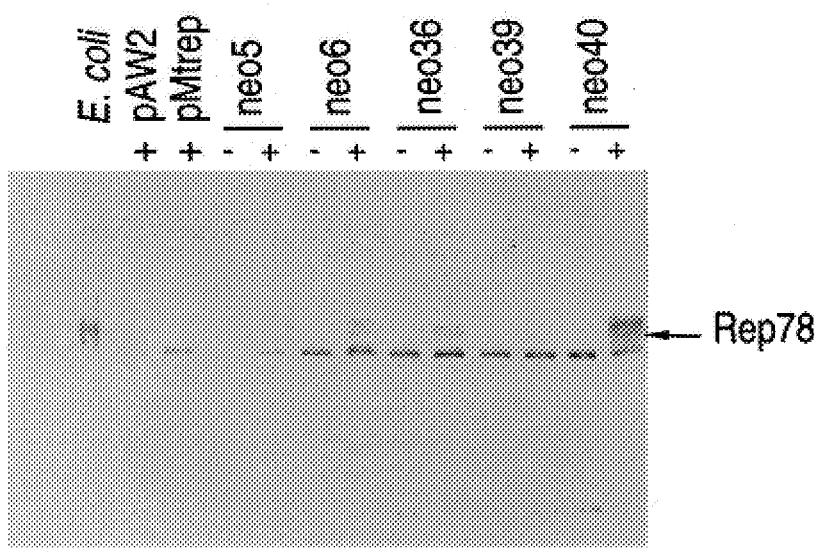
FIG. 2 is a half-tone reproduction of Western blot analysis of Rep proteins from various neomycin-resistant clones cultured in the absence (−), or presence (+), of heavy metal induction, or from 293 cells transfected with pAW2 of pMtrep. Lane *E. coli* contains Rep protein from a prokaryotic expression vector.

Cultures were grown in selective medium for 10 to 14 days, after which the surviving colonies were isolated, cultured and assayed for Rep protein expression. To induce Rep protein expression, the cell culture medium was adjusted to 2 µm $CdSO_4$ and 100 µm $ZnCl_2$ 16–24 hours before the cultures were harvested and analyzed for Rep protein expression. Western blot analysis to detect Rep expression was performed using Rep-specific antiserum (Trempe et al. 1987. *Virology* 161:18–28) as described below. One clone, Neo6, was found to express significant amounts of Rep78 as determined by Western blot assays using anti-Rep antiserum (FIG. 2). Another geneticin-resistant clone, neo5, did not express any detectable Rep protein upon induction. Indirect immunofluorescence of Neo6 cells indicated that between 30–70% of the cells were positive for Rep protein expression (Yang and Trempe, Unpublished data).

In an attempt to obtain a higher percentage of Rep-positive cells, Neo6 cells were subcloned by limiting dilution. Subcloning of Neo6 generated clones Neo34, Neo36, Neo39 and Neo40, which all produce significant levels of Rep78 when induced (FIG. 2). Although clone Neo34 is not shown on this western blot it produced Rep78 at level comparable to that of Neo6 (Yang and Trempe, ibid.). The proportion of cells expressing Rep proteins among the subclones was comparable to that of the parental Neo6 cells (approximately 60%) as judged by immunofluorescence, and the staining was also confined to the nucleus (Yang and Trempe, ibid.).

Protein extraction and analysis $3 \times 10^5$ geneticin-resistant cells in 35 mm dishes were induced for the expression of Rep proteins. Rep proteins from the cell lines or transfected cells were extracted from nuclei in 200 mM NaCl in STM-NP buffer as previously described (Yang, ibid.). The protein extracts were separated by sodium dodecyl sulfate 12.5% polyacrylamide gel electrophoresis (SDS-PAGE) and analyzed by Western immunoblotting as previously described (Yang et al. 1992. *J. Virol.* 66:6058–6069) or were used in gel mobility shift assays.

Gel mobility shift assay

Figure 3:
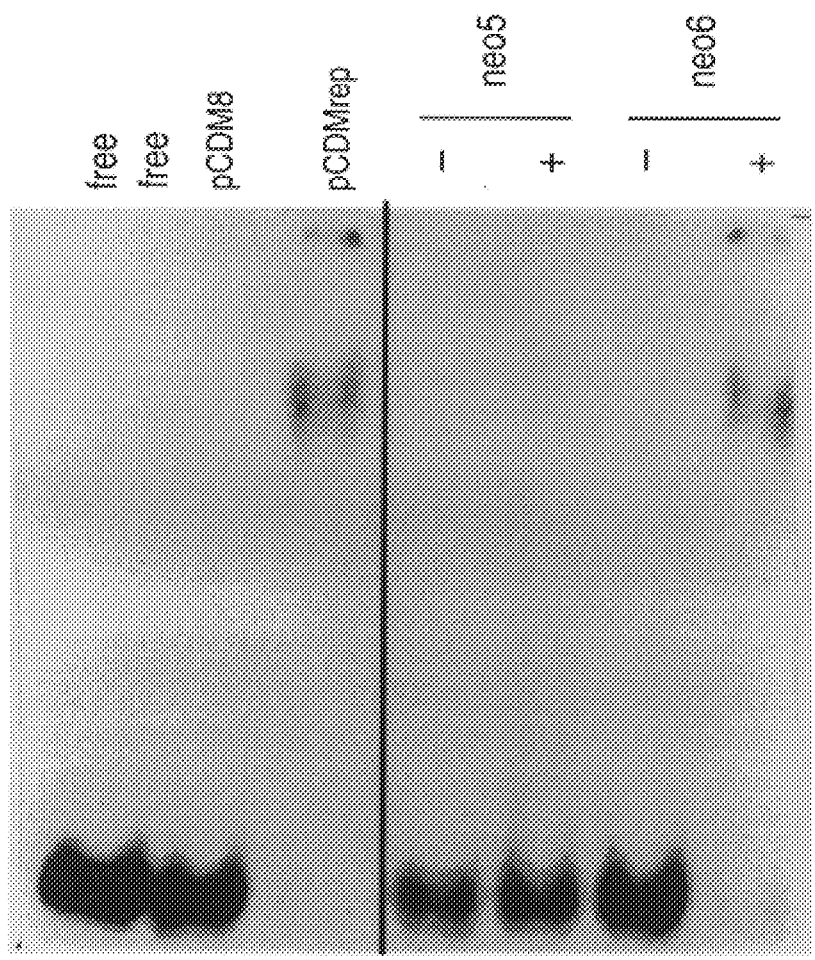
FIG. 3 is a half-tone reproduction of AAV terminal repeat binding assay using Rep78 produced from neo6 cells. The DNA binding reaction contained no extract (lane free), or 1

Rep78 mediates AAV DNA replication by binding to the AAV terminal repeat sequences existing in a hairpin conformation and this characteristic can be emulated in vitro (Asktorab and Srivastave. 1989. *J. Virol.* 63:3034–3039; Im and Muzyczka. 1989. *J. Virol.* 63:3095–3104). The following hairpin binding assays were performed to establish that Rep78 from Neo6 cells is functional. 5,000 cpm radiolabelled AAV hairpin was used in each reaction. FIG. 3 shows an AAV hairpin binding assay with nuclear extracts from Neo5, Neo6 and wild type rep gene plasmid-transfected cells. Rep78 protein produced from induced Neo6 cells efficiently bound to the radiolabeled hairpin; whereas, no mobility shift was observed with nuclear extracts from uninduced Neo6 cells. This is consistent with the Western blotting analysis of Neo6 cells where no Rep78 was detected in the absence of induction (FIG. 2). The shifted band can be abolished by the addition of excess unlabeled AAV hairpin or supershifted by antibody against the Rep proteins (Yang and Trempe, Unpublished data).

As a positive control for these mobility shift assays, nuclear extracts were prepared from pCDMrep-transfected 293 cells which are known to contain Rep78 that efficiently binds to the AAV terminal repeat sequences (Yang and Trempe. 1993. *J. Virol.* 67:4442–4447). Nuclear extracts from plasmid pCDM8-transfected 293 cells or control clone Neo5 failed to shift the hairpin structure. Binding of the Rep78 protein to radiolabeled AAV hairpin DNA was performed as described previously (Yang and Trempe, ibid.). Rep78 produced from these cell lines has similar mobilities after binding as Rep78 from human 293 cells transfected with pMtrep, and the bound proteins appear as a doublet, as observed by others (Im and Muzyczka. 1992. *J. Virol.* 66:1119–1128).

The predominant form of Rep protein expressed in these cells is Rep$^7$8. This may be due to the absence of helper virus infection which enables efficient AAV mRNA splicing which in turn would limit Rep68 synthesis (Trempe and Carter. 1988. *J. Virol.* 62:3356–3363). The lack of Rep52 expression may also be due to the absence of adenovirus infection which has been shown to increase $p_{19}$ expression (Tratschin et al. 1984. *Mol. Cell. Biol.* 4:2072–2081), or the lack of AAV terminal repeat sequences which also have a stimulatory effect on $p_{19}$ expression (Beaton et al. 1989. *J. Virol.* 63:4450–4454).

AAV DNA replication and packaging assays

For determination of AAV DNA replication, 2 µg of pJDT279 was transfected into the indicated cell lines in the presence of adenovirus type 2 coinfection (MOI=5). Two days after transfection, Hirt supernatant DNA was prepared it. 1967. *J. Mol. Biol.* 26:365–369). The DNA was then digested with DpnI, separated by agarose gel electrophoresis, transferred to nitrocellulose filter paper, hybridized to a radiolabeled AAV cap gene probe and processed by autoradiography using standard techniques (Ausubel et al. (ed.) 1987. *Current Protocols in Molecular Biology.* Greene Publishing Associates, Brooklyn, N.Y.). The hybridization probe was a HincII restriction endonuclease fragment from pJDT279 that contained sequences from 2397 to 3981 of the AAV genome.

Example 3

Packaging of Recombinant AAV Vectors

Current methods of producing infectious, mutant AAV particles utilize cotransfections of an AAV vector plasmid containing the viral origins of replication and a plasmid containing the rep and cap genes of AAV. A limitation of this method is that if there are any homologous sequences shared between the two cotransfected plasmids, substantial recombination will occur resulting in production of wild type AAV. Thus, care must be taken to avoid overlapping homologies between the two transfected plasmids.

pYT45 contains the AAV terminal repeat sequences, the bacterial cat gene driven by the AAV p5 transcription promoter and the AAV polyadenylation signal (Khlief et al. 1991. *Virology* 181:738–741). For packaging of pYT45 into an infectious virion, p1097cap was used to provide the cap gene sequences which provide capsid proteins for assembly of the AAV virion. p1097cap does not produce any of the Rep proteins due to the lack of the p5 transcription promoter and a 12 bp XhoI oligonucleotide linker that is inserted at nucleotide 1097 of the AAV rep gene sequences. p1097cap contains AAV sequences from nucleotide 263 to 4493 inserted into the pGEM3Z plasmid (Promega Corp.).

For the packaging of pYT45 sequences, 10 µg of p1097cap and 5 µg of pYT45 were cotransfected onto $5 \times 10^5$ cells of each cell line that had been infected with adenovirus and induced with cadmium and zinc salts. Two days after transfection, the packaged pYT45, vYT45, was harvested as described above and used to infect new cultures ($5 \times 10^5$ cells) of the same cell lines from which they were derived, after the cultures had been induced with heavy metal and infected with adenovirus. Two days after infection, the cultures were harvested, extracts prepared and half of the extract from $5 \times 10^5$ cells was used for Cat enzyme assays (Ausubel et al. (ed.) 1987. *Current Protocols in Molecular Biology.* Greene Publishing Associates, Brooklyn, N.Y.). The percentage acetylation of chloramphenicol was determined by scintillation counting of the thin layer chromatography plates.

To package rep gene mutant AAVs, 10 µg of pJDT279 was transfected into $5 \times 10^5$ adenovirus-infected Rep-producing cells that had been induced with heavy metals. Two days later, the cultures were harvested by scraping the cells into phosphate buffered saline (PBS) containing 5 mM $MgCl_2$, frozen and thawed three times, heated at 60° C. for 30 minutes to inactivate the adenovirus and then treated for 30 minutes at 37° C. with 100 Units/ml of pancreatic DNaseI (Sigma Chemical Corp.). The extract was centrifuged at 10,000× g for 20 minutes at 4° C., and the supernatant was used for subsequent infections. The extracts were used to infect new cultures ($5 \times 10^5$ cells) of the same cell lines from which they were derived after the cultures had been induced with cadmium and zinc salts as described above and infected with adenovirus. Two days later, the cultures were harvested, Hirt DNA preparations performed and analyzed by agarose gel electrophoresis and Southern hybridizations with the same radiolabeled cap gene probe that was used for the DNA replication assays.

To determine if the Rep-inducible cell lines were capable of producing infectious progeny bearing a rep gene mutation, the plasmid pJDT279 was transfected onto the heavy metal-induced cell lines that had been infected with adenovirus. Two days later, the cultures were harvested, and crude cell extracts were prepared as described above. The extracts were then used to infect new cultures had been induced with heavy metal and infected with adenovirus. Two days later, the cultures were harvested, Hirt DNA preparations performed and analyzed by agarose gel electrophoresis and Southern hybridizations with a radiolabeled cap gene probe. In FIG. 4 the pMtrep lane contains DNA from 293 cells that had been infected with vJDT279 that had been produced by cotransfection of pMtrep and pJDT279 onto adenovirus-infected 293 cells. The pJDT279 lane contains a partial BglII digestion of the plasmid producing linearized plasmid and monomer-length DNA. The locations of dimer (D) and monomer (M) replicative form and single strand (SS) DNAs are indicated. From FIG. 4, it is apparent that all of the Rep-producing cell lines directed the assembly of infectious AAV containing a mutant rep gene. (Replicative form (RF) monomer DNA could be observed in the Neo40 lane upon longer exposure of the autoradiogram.)

No infectious virus was amplified in the absence of induction indicating that there was no detectable production of wild type virus produced during the initial transfection. As expected, Neo5 cells did not yield any infectious virus under either induced or noninduced conditions. As a control for these experiments, pMtrep was cotransfected with pJDT279 onto adenovirus-infected 293 cells and progeny virus harvested. After subsequent infection of adenovirus-infected 293 cells, it is apparent that wild type AAV was generated from the initial cotransfection of pJDT279 and pMtrep. A significant amount of RF DNA was observed which is indicative of recombination between the common rep gene sequences between pMtrep and pJDT279. These experiments indicate that the Rep-producing cell lines provide an improved method for generating infectious rep gene mutant virus without producing wild type AAV from recombination.

MTT growth assay

Comparison of the growth rates under induced and uninduced conditions for neo5, neo6, and neo40 cells was made using MTT growth inhibition assays.

$1 \times 10^3$ Neo5, Neo6 or Neo40 cells were seeded into each well of a 24-well dish. Twenty-four hours after plating, the medium on half of the cultures was changed to include cadmium and zinc salts. At 2, 4, 8 and 12 days after plating, the medium was replaced with serum-free, phenol red-free MEM containing 0.05 mg/ml MTT (3-(4,5-dimethylthiazol-2-yl)2,5-diphenyl tetrazolium bromide; Sigma Chemical Co.). The cultures were then incubated for an additional 4 hrs at 37° C. in a humidified 5.0% $CO_2$ atmosphere. The medium was then removed by aspiration and the cultures treated with 200 μl of stop solution (0.04N HCl in isopropanol). The plates were shaken vigorously for one hour to dissolve the formazan crystals. Absorbance (at 595 nm) of the stop solution was determined. Stock MTT solutions were prepared by first dissolving MTT in PBS, pH 7.5, at a concentration of 5 mg/ml. The solution was filtered with 0.45μ syringe filters to remove any undissolved crystals.

Upon induction of rep gene expression, both neo6 and neo40 cells grew much more slowly than did the uninduced cultures (FIG. 6). In contrast, the control neo5 cells were not inhibited by heavy metal induction. Between the eighth and twelfth days, both neo6 and neo40 cells seemed to begin growing again. This may be due to loss of Rep protein expression or cellular acclimation to the presence of Rep proteins. Immunofluorescent staining using anti-Rep antibodies of the induced cultures up to fourteen days after induction revealed that 50–60% of the cells still contained Rep protein (Yang and Trempe, Unpublished data). This percentage is similar to that of neo6 or neo40 cells after a two-day induction.

Example 4

Production of Stable Cell Lines

The Neo6 and Neo40 cell lines have been cultured for more than ten months and more than 50 generations. The abilities of these cells to produce the Rep proteins upon induction has not diminished over this period of time. Both cell lines have retained inducibility, and there is no change in the population of cells that are responsive to heavy metal induction as measured by Rep protein production (Yang and Trempe, Unpublished data). A critical period in the development of the cell lines was observed from passage 10 to 15, during which time the cells of inducible cell lines could not be trypsinized and replated at low density (more than 1 to 3 dilution). After this crisis period, the clones can be maintained as established cell lines with the exception of subclone Neo34, which could not be cultured beyond 20 passages. Clone Neo34 expressed detectable amounts of Rep protein and behaved similarly in functional assays to other clones (Yang and Trempe, Unpublished data).

Colony-formation efficiency (CE) assay

The presence of AAV DNA sequences results in altered growth properties of infected cells, and in some cases arrests cell growth. To determine the effects of the Rep protein on the cell lines, the growth rates and colony formation efficiency of the neo 5, neo6 and neo40 cell lines were determined. The doubling times of the Rep-inducible cells (as measured by trypan blue exclusion) indicated that they multiplied more slowly than neo5 cells with doubling times of about 35 hours for neo 5, 43 hours for neo6, and 50 hours for neo40 (Yang and Trempe, Unpublished data).

$1 \times 10^3$ Neo5, Neo6 and Neo40 cells were sparsely plated on 6 cm dishes in triplicate to test their cloning efficiency in the presence and absence of Rep protein expression. Two of the three cultures in each set contained cadmium and zinc salts in the medium, and the third contained normal medium. After 14 days' incubation, the uninduced culture and one induced culture from each set were fixed in 18% formaldehyde in PBS and stained with crystal violet as described previously (Yang et al. 1992. *J. Virol.* 66:6058–6069). The heavy metal-containing medium on the third culture in each set was replaced with normal medium, and those cultures were incubated for an additional 14 days. These 28-day cultures were then fixed and stained, and the number of foci were counted. Foci larger than 2 mm were counted.

Heavy metal induction (accompanied by Rep synthesis) had a moderate inhibitory effect on the CFE of neo5 cells (FIG. 5). Two weeks after incubation, the induced (B,D,G) and uninduced (A,C,F) plates stained. The remaining plates (E,H) were recultured in normal medium for an additional two weeks and then stained. However, the growth of the Rep78-expressing cells was drastically reduced in the presence of induction. For both neo6 and neo40 cells, there was a greater than 90% reduction of CFE in the presence of Rep78. When Rep78 was expressed, very few colonies from neo6 and neo40 formed foci that were visible without magnification.

Microscopic examination of the plates before sting revealed that those cells which failed to grow into clusters were morphologically normal (Yang and Trempe, Unpublished data). Some of the large foci from induced neo6 cells were recultured (with induction) and assayed by indirect immunofluorescence using Rep-specific antibody to determine if they retained the ability to express Rep protein. All of the clones tested showed similar levels of immunofluorescence as neo6 cells that had been induced for two days (Yang and Trempe, Unpublished data).

Flow cytometry analysis

The AAV Rep78 protein inhibits SV40 DNA replication in 293 and COS-1 cells and cellular DNA synthesis in NIH3T3 cells (Yang et al. Manuscript submitted to *J. Virol.*). The inhibition may be due to either direct interference of cellular DNA replication or inhibition of cell cycle progression by the Rep protein. To investigate these two possibilities, flow cytometry was performed on the inducible cell lines as follows. $2 \times 10^6$ cells of Neo6, neo40 and control neo5 cells were plated in 15 cm dishes in the presence or absence of heavy metals. After 72 hours of incubation, cells were rinsed with PBS and stored in liquid nitrogen in citrate buffer (250 mM sucrose and 40 mM sodium citrate) containing 5% DMSO, at a concentration of $5 \times 10^6$ cells/ml. Propidium iodide staining was performed as described (Vindelov et al. 1983. *Cytometry* 3:323–327). Flow cytometry was preformed on a Colter flow cytometer. The population of cells in different stages of the cell cycle was calculated with a second order polynomial fit using the Multicycle software described by Peter S. Rabinovitch (Phoenix Flow System).

Table 1 summarizes the results. Heavy metals have no effects on the cell cycle progression in neo5 cells, as demonstrated by the similar percentages of cells in the G1, G2, and S phases of cell cycle (Table 1). Clone neo40, however, showed a significant increase in the number of cells in the S phase when the Rep protein was induced. Neo6 cells also displayed a modest increase of cells in S phase upon induction. Without induction, neo5 cells had fewer cells in the S phase, than did neo40 or neo6 cells. This effect may be due to low levels of Rep protein that remain undetectable in the uninduced state. If so, low level Rep protein expressed from uninduced metallothionein promoter may exert an inhibitory effect. No sharp peak was observed at any point in S phase. Instead, the increase was distributed throughout the whole process of DNA synthesis indicating that Rep78 does not introduce a cycle block, but rather it slows the progress of the cell through the DNA synthetic phase. These results suggest that the Rep proteins' antiproliferative effects probably stem from inhibition or slowing of DNA synthesis instead of introducing a cell cycle block in the G1, G2 or M phases.

TABLE 1

Cell cycle distribution of induced and uninduced clones.[A]

| Cell line | G1 | S | G2/M |
|---|---|---|---|
| Neo5 (−) | 62.3 ± 1.4 | 24.9 ± 2,1 | 12.9 ± 2.3 |
| Neo5 (+) | 60.0 ± 1.0 | 23.4 ± 3.3 | 16.7 ± 2.6 |
| Neo6 (−) | 61.2 ± 15.8 | 32.9 ± 8.2 | 6.0 ± 1.8 |
| Neo6 (+) | 56.4 ± 10.2 | 37.4 ± 9.8 | 6.2 ± 0.6 |
| Neo40 (−) | 50.2 ± 4.5 | 38.5 ± 4.3 | 11.3 ± 0.8 |
| Neo40 (+) | 36.8 ± 0.9 | 53.9 ± 1.6 | 9.3 ± 0.2 |

[A]The indicated cell lines were plated at a density of $2 \times 10^6$ cells in the absence (−) or presence (+) of heavy metal salts on 15 cm dishes. 72 hrs after plating, the cells were harvested as described in the text and analyzed by flow cytometry. The percentages of cells in the indicated phases of the cell cycle ± standard deviation are given. The results are a compilation of four experiments.

We claim:

1. A stable mammalian cell line with an adeno-associated virus (AAV) rep gene operably linked to a heterologous promoter, which cell line contains a gene encoding functional Rep protein.

2. The cell line of claim 1, wherein the line is human 293 cells which contain a gene encoding functional Rep protein operably linked to a heterologous promoter.

3. The cell line of claim 2 wherein the heterologous promoter is a murine metallothionein I gene promoter.

4. The cell line of claim 1 wherein the promoter consists of a fragment of the murine metallothionein I gene from approximately −650 bp from the transcription start site of the gene to a 69 bp downstream of said site.

5. A cell line of claim 2 designated Neo6.

6. A method of packaging a recombinant AAV vector without producing wild-type AAV, said method comprising
    (a) transfecting a cell line of claim 1, wherein said cell line is infected with a helper virus, with a recombinant plasmid containing an AAV vector, said vector either having a functional AAV capsid gene or being complemented with a second vector having a functional capsid gene, wherein said AAV vector lacks overlapping homology with AAV sequences in the cell provided in claim 1, resulting in transfected cells; and
    (b) culturing the transfected cells under conditions that permit expression of the AAV rep and cap genes.

7. A method of packaging a recombinant AAV vector without producing wild-type AAV comprising
    (a) transfecting a cell line of claim 2, wherein said cell line is infected with a helper virus, with a recombinant plasmid containing an AAV vector, said vector either having a functional AAV capsid gene or being complemented with a second vector having a functional capsid gene, wherein said AAV vector lacks overlapping homology with AAV sequences in the cell provided in claim 2, resulting in transfected cells; and
    (b) culturing the transfected cells under conditions that permit expression of the AAV rep and cap genes.

8. A method of packaging a recombinant AAV vector without producing wild-type AAV comprising
    (a) transfecting a cell line of claim 3, wherein said cell line is infected with a helper virus, with a recombinant plasmid containing an AAV vector, said vector either having a functional AAV capsid gene or being complemented with a second vector having a functional capsid gene, wherein said AAV vector lacks overlapping homology with AAV sequences in the cell provided in claim 3, resulting in transfected cells; and
    (b) culturing the transfected cells under conditions that permit expression of the AAV rep and cap genes.

9. A method of packaging a recombinant AAV vector without producing wild-type AAV comprising
   (a) transfecting a cell line of claim 4, wherein said cell line is infected with a helper virus, with a recombinant plasmid containing an AAV vector, said vector either having a functional AAV capsid gene or being complemented with a second vector having a functional capsid gene, wherein said AAV vector lacks overlapping homology with AAV sequences in the cell provided in claim 4, resulting in transfected cells; and
   (b) culturing the transfected cells under conditions that permit expression of the AAV rep and cap genes.

10. A method of packaging a recombinant AAV vector without producing wild- type AAV comprising
    (a) transfecting a cell line of claim 5, wherein said cell line is infected with a helper virus, with a recombinant plasmid containing an AAV vector, said vector either having a functional AAV capsid gene or being complemented with a second vector having a functional capsid gene, wherein said AAV vector lacks overlapping homology with AAV sequences in the cell provided in claim 5, resulting in transfected cells; and
    (b) culturing the transfected cells under conditions that permit expression of the AAV rep and cap genes.

11. A method of reinfecting the cell line of claim 1 with particles without producing wild-type AAV, said method comprising
    (a) infecting a cell line of claim 1 wherein said cell line is infected with a helper virus, with a recombinant AAV particle, said particle containing a vector either having a functional AAV capsid gene or being complemented with a second vector having a functional capsid gene, resulting in infected cells; and
    (b) culturing the infected cells under conditions that permit expression of the AAV rep and cap genes.

12. A method of reinfecting the cell line of claim 2 with particles without producing wild-type AAV, said method comprising
    (a) infecting a cell line of claim 2 wherein said cell line is infected with a helper virus, with a recombinant AAV particle, said particle containing a vector either having a functional AAV capsid gene or being complemented with a second vector having a functional capsid genes resulting in infected cells; and
    (b) culturing the infected cells under conditions that permit expression of the AAV rep and cap genes.

13. A method of reinfecting the cell line of claim 3 with particles without producing wild-type AAV, said method comprising
    (a) infecting a cell line of claim 3 wherein said cell line is infected with a helper virus, with a recombinant AAV particle, said particle containing a vector either having a functional AAV capsid gene or being complemented with a second vector having a functional capsid gene, resulting in infected cells; and
    (b) culturing the infected cells under conditions that permit expression of the AAV rep and cap genes.

14. A method of reinfecting the cell line of claim 4 with particles without producing wild-type AAV, said method comprising
    (a) infecting a cell line of claim 4 wherein said cell line is infected with a helper virus, with a recombinant AAV particle, said particle containing a vector either having a functional AAV capsid gene or being complemented with a second vector having a functional capsid gene, resulting in infected cells; and
    (b) culturing the infected cells under conditions that permit expression of the AAV rep and cap genes.

15. A method of reinfecting the cell line of claim 5 with particles without producing wild-type AAV, said method comprising
    (a) infecting a cell line of claim 5 wherein said cell line is infected with a helper virus, with a recombinant AAV particle, said particle containing a vector either having a functional AAV capsid gene or being complemented with a second vector having a functional capsid gene, resulting in infected cells; and
    (b) culturing the infected cells under conditions that permit expression of the AAV rep and cap genes.

16. A method for producing the cell line of claim 1 comprising
    (a) transfecting a mammalian cell line capable of infection by AAV with an AAV vector having the AAV rep gene operably linked to an AAV replication protein 78 insensitive transcription promoter, to produce transfected cells;
    (b) culturing the transfected cells under conditions that permit expression of the gene;
    (c) selecting a cell that stably produces said protein; and
    (d) growing said cell to produce the cell line.

17. A stable mammalian cell line with an adeno-associated virus )AAV) rep gene operably linked ti a relatively Rep78-insensitive homologous transcription promoter, which cell line contains a gene encoding functional Rep protein.

18. A method for producing the cell line of claim 17 comprising
    (a) transfecting a mammalian cell line capable of infection by AAV with an AAV vector having the AAV replication gene operably linked to an AAV replication protein 78 insensitive transcription promoter, to produce transfected cells;
    (b) culturing the transfected cells under conditions that permit expression of the gene;
    (c) selecting a cell that stably produces said protein; and
    (d) growing said cell to produce the cell line.

* * * * *

UNITED STATES PATENT AND TRADEMARK OFFICE

CERTIFICATE OF CORRECTION

PATENT NO. : 5,837,484

DATED : November 17, 1998

INVENTOR(S) : James P. Trempe and Qicheng Yang

It is certified that errors appear in the above-identified patent and that said Letters Patent is hereby corrected as shown below:

Claim 12, line 8, "gene" should read -- gene, --

Claim 17, line 2 should read "associated virus (AAV) rep gene operably linked to a rel-"

Signed and Sealed this

Thirtieth Day of March, 1999

Attest:

Attesting Officer

Q. TODD DICKINSON

Acting Commissioner of Patents and Trademarks